(12) United States Patent
Eger

(10) Patent No.: US 8,109,269 B2
(45) Date of Patent: Feb. 7, 2012

(54) METHOD OF AUTOMATICALLY CONTROLLING A RESPIRATION SYSTEM AND A CORRESPONDING RESPIRATOR

(75) Inventor: Marcus Eger, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 751 days.

(21) Appl. No.: 12/264,993

(22) Filed: Nov. 5, 2008

(65) Prior Publication Data

US 2009/0159082 A1 Jun. 25, 2009

(30) Foreign Application Priority Data

Dec. 21, 2007 (DE) .................. 10 2007 062 214

(51) Int. Cl.
*F16K 31/02* (2006.01)
(52) U.S. Cl. .......... 128/204.23; 128/204.21; 128/200.14
(58) Field of Classification Search ............. 128/204.18, 128/204.21–204.23, 203.12, 203.13; 600/529, 600/534–536, 538, 484, 546, 547
See application file for complete search history.

(56) References Cited

U.S. PATENT DOCUMENTS

| | | | |
|---|---|---|---|
| 5,107,830 A | 4/1992 | Younes | |
| 5,820,560 A | 10/1998 | Sinterby et al. | |
| 5,884,622 A | 3/1999 | Younes | |
| 6,820,613 B2 | 11/2004 | Wenkebach et al. | |
| 6,837,241 B2 * | 1/2005 | Samzelius | 128/204.21 |
| 7,021,310 B1 | 4/2006 | Sinderby | |
| 7,661,427 B2 * | 2/2010 | Sinderby et al. | 128/204.21 |
| 7,934,499 B2 * | 5/2011 | Berthon-Jones | 128/204.23 |

FOREIGN PATENT DOCUMENTS

| | | |
|---|---|---|
| GB | WO 97/22377 | 6/1997 |
| WO | WO 2006/131149 A1 | 12/2006 |

OTHER PUBLICATIONS

Magdy Younes; Proportional Assist Ventilation; Alternative Methods of Ventilator Support, Chapter 15, pp. 348-369.
C. Sinderby, L. Brander, and J. Beck; Is One Fixed Level of Assist sufficient to Mechanically Ventilate Spontaneously Breathing Patients?; Yearbook 2007, pp. 348-357.
Christer Sinderby, PhD; Jennifer Beck, PhD; Jadranka Spahija, PhD; Michel de Marchie, MD; Jacques Lacrois, MD; Paolo Navalesi, MD; and Arthur S. Slutsky, MD; Chest, Original Research, Critical Care Medicine, www.chestjournal.org, Mar. 2007, pp. 711-717.

(Continued)

*Primary Examiner* — Glenn Richman
(74) *Attorney, Agent, or Firm* — McGlew and Tuttle, P.C.

(57) ABSTRACT

A method of automatically controlling a respiration system for proportional assist ventilation with a control device and with a ventilator. An electrical signal is recorded by electromyography with electrodes on the chest in order to obtain a signal $u_{emg}(t)$ representing the breathing activity. The respiratory muscle pressure $p_{mus}(t)$ is determined by calculating it in the control unit from measured values for the airway pressure and the volume flow Flow(t) as well as the patient's lung mechanical parameters. The breathing activity signal $u_{emg}(t)$ is transformed by means of a preset transformation rule into a pressure signal $p_{emg}(u_{emg})(t))$ such that the mean deviation of the resulting transformed pressure signal $p_{emg}(t)$ from the respiratory muscle pressure $p_{mus}(t)$ is minimized. The respiratory effort pressure $p_{pat}(t)$ is determined as a weighted mean according to $p_{pat}(t)=a \cdot p_{mus}(t)+(1-a) \cdot p_{emg}(t)$, where a is a parameter selected under the boundary condition $0 \leq a \leq 1$.

37 Claims, 10 Drawing Sheets

OTHER PUBLICATIONS

Christer Sinderby, Paolo Navalesi, Jennifer Beck, Yoanna Skrobik, Normal Comtois, Sven Friberg, Stewart B. Gottfried and Lars Lindstrom; Neural Control of Mechanical Ventilation in Respiratory Failure; New Technology, Nature Medicine, vol. 5, No. 12, Dec. 1999, pp. 1433-1436.

Maarsingh et al., "Respiratory muscle activity measured with a noninvasive EMG technique: technical aspects and reproducibility", The American Physiological Society, 2000, pp. 1955-1961.

Tarata et al, The Accelerometer MMG Measurement Approach, in Monitoring the Muscular Fatigue, Measurement Science Review, 2001, vol. 1, No. 1, pp. 47-50.

* cited by examiner

METHOD OF AUTOMATICALLY CONTROLLING A RESPIRATION SYSTEM AND A CORRESPONDING RESPIRATOR

CROSS REFERENCE TO RELATED APPLICATIONS

This application claims the benefit of priority under 35 U.S.C. §119 of German Patent Application DE 10 2007 062 214.9 filed Dec. 21, 2007, the entire contents of which are incorporated herein by reference.

FIELD OF THE INVENTION

The present invention pertains to a method and a device for automatically controlling a respiration system (also known as ventilation system) for proportional assist ventilation, with a control means and with a ventilator, which delivers a breathing gas with a pressure preset by the control unit.

BACKGROUND OF THE INVENTION

Methods that assist the patient proportionally to his or her own respiratory effort and relieve the patient of the increased work of breathing in order to thus prevent exhaustion of the respiratory muscles and the so-called respiratory failure have been developed in recent years for respirating spontaneously breathing patients. Compared to conventional forms of respiration, the form of respiration called proportional assist ventilation offers a relief for the respiratory muscles, it guarantees a physiological breathing pattern and increases the patient's comfort, e.g., due to improved sleep.

Two fundamentally different concepts are known for the proportional assist ventilation methods: the so-called "Proportional Assist Ventilation" (PAV) and methods with "Naturally Adapted Ventilatory Assist" (NAVA).

In methods with "Proportional Assist Ventilation" (c.f., e.g., Younes, M.: Proportional Assist Ventilation, in: Tobin M. J., ed.: Principles and practice of mechanical ventilation, New York, McGraw-Hill, 1994, pp. 349-369), a pressure assist is generated, which contains a percentage proportional to the currently present volume flow (flow) as well as a percentage proportional to the volume. The degree of assist is preset by the setting values Flow Assist (FA) and Volume Assist (VA). Due to the positive feedback of the volume flow and the volume, this form of respiration embodies a kind of servo control, which makes it possible separately to compensate percentages of the resistive and elastic resistances of the breathing system and thus to quantitatively relieve the patient of the work of breathing. However, a sufficiently accurate estimated value must be available for this for the actual resistance® and elastance (E), because instabilities (so-called runaways) and possible damage to the lungs due to barotrauma may otherwise develop.

Furthermore, efforts have been made for quite some time now to determine R and E during spontaneous breathing reliably and in a minimally invasive manner (cf., e.g., WO 97/22377 A1). The special difficulty is due to the fact that the patient's spontaneous breathing activities may cause great errors in determining the breathing technical parameter. A usual procedure is the introduction of interference maneuvers into the breathing pattern (e.g., by a short-term occlusion) at points in time at which a passive phase of breathing is suspected, and the subsequent analysis of the disturbed respiratory signals. However, it is not guaranteed that the patient is in an undisturbed phase of the breathing cycle at the time of the maneuver, and the validity of the measurement is therefore not guaranteed; it also cannot be demonstrated later. This is due to the circumstance that the activity of the respiratory muscles cannot be separated from the mechanical respiration pattern based on close correlations either on the basis of signal theory or statistically.

In methods with "Naturally Adapted Ventilatory Assist" (NAVA), as described, e.g., in: Sinderby et al.: Is one fixed level of assist sufficient to mechanically ventilate spontaneously breathing patients?, Yearbook of intensive care and emergency medicine, 2007, Springer 348-367; Sinderby et al.: Neural control of mechanically ventilation in respiratory failure, *Nature Medicine,* 1999 (5), 12: 1433-1436, the electrical activity of the diaphragm (EAdi) is recorded by means of a modified gastric probe equipped with electrodes in order to regulate the pressure assist of the ventilator in proportion to this electrical activity. Interference signals (e.g., ECG) are filtered out in advance. The advantages of NAVA are improved interaction between the patient and the ventilator due to synchronized ventilation and the physiological breathing pattern associated therewith. It was demonstrated in a more recent study (Sinderby et al.: Inspiratory muscle unloading by neurally adapted ventilatory assist during maximal inspiratory efforts in healthy subjects, *Chest,* 2007, 131: 711-717) that a relief of the work of breathing is achieved by an adapted setting of the so-called NAVA level (amplification factor that defines the pressure level relative to EAdi) and overexpansion of the lungs is avoided, because the EAdi signal decreases at high NAVA level. As a result, the risk of run-away decreases. Unlike in the case of the usual pressure assist, there are no fundamental problems with the triggering of a respiration stroke ("triggering") in patients with dynamic hyperinflation (e.g., in patients with chronic obstructive pulmonary disease (COPD)), because a possible intrinsic peak end-expiratory pressure (PEEP) represents no obstacle thereto. Termination of the inspiration ("cycling off") is likewise unproblematic.

One drawback of the NAVA method is that an invasive gastric probe is necessary. Patients who would especially benefit from the use of NAVA methods (e.g., patients with COPD subjected to long-term noninvasive respiration, i.e., respiration with a mask), will dislike accepting such a permanent solution. Furthermore, it is not possible to make a distinction between a situation in which the EAdi signal is compromised for technical reasons inherent in the device (e.g., due to interference signals or faulty coupling between the signal source and the electrodes) and a situation in which the respiratory drive decreases. The requirement that the patient be relieved of a certain amount of work of breathing can therefore be achieved only qualitatively. If the coupling between the signal source (EAdi signal of the muscles) and the electrodes changes, this affects the work of breathing to be performed by the patient. The respiratory pressure is usually controlled in direct proportion to the EAdi signal processed. If the EAdi signal increases (e.g., due to increased respiratory drive), the increased respiration by the ventilator leads, on a rather long-term basis, to a reduction of the respiratory drive and correspondingly of the EAdi signal. This negative feedback becomes stabilized at a certain EAdi signal level. If the coupling between the signal source and the electrodes changes—e.g., deteriorates—in this equilibrium, the tidal volume is reduced, the drive and the respiratory effort gradually increase, but the measured EAdi signal decreases, which means that the percentage of the work of breathing performed by the patient increases in an undesired manner.

A special proportional assist NAVA method using a signal for the electrical activity of the diaphragm is known from U.S. Pat. No. 7,021,310 B1; the peculiarity of this method is that the electrical activity of the diaphragm, which is needed for a certain tidal volume (the so-called neuroventilatory efficiency), is said to be maintained at a constant value by means of a "closed-loop" control. In case the patient's properties in terms of the mechanics of breathing worsen, the respiratory effort (and hence the activity of the respiratory muscles) increase to maintain the tidal volume per unit of time. The "closed-loop" controller would counteract this by increasing the assist, so that the EAdi signal level remains unchanged and overloading/exhaustion of the patient is avoided. This method is disadvantageous in the case that frequently occurs in reality, in which the signal properties (especially the amplitude) of the measured EAdi signal change, e.g., decrease due to a change in the coupling between the electrodes and the signal source (caused, e.g., by repositioning of the patient). The controller of the "closed-loop" system would consequently erroneously reduce the assist, because the neuroventilatory efficiency has seemingly increased.

SUMMARY OF THE INVENTION

The object of the present invention is to provide a method of automatically controlling a respiration system for proportional assist ventilation, which is convenient for the patient and operates precisely over the long term, as well as to propose a correspondingly operating respirator.

In a method for automatically controlling a respiration system for proportional assist ventilation with a control means and with a ventilator (including a gas delivery means), which delivers a breathing gas with a pressure preset by the control unit, an electrical signal is accordingly recorded on the chest by electromyography or an electrical signal is generated by sensors on the chest by mechanomyography and subjected to signal processing in the control means in order to obtain a signal $u_{emg}(t)$ representing the breathing activity. The rate of change (time derivative) $\dot{u}_{emg}(t)$ of the breathing activity signal $u_{emg}(t)$ is formed in the control unit and checked continuously to determine if it is below a threshold value criterion, and a period of the breathing cycle that is constant with respect to the breathing activity is established for the duration of the period during which said signal is below the threshold value.

The respiratory muscle pressure $p_{mus}(t)$ is determined as follows: (I) It is calculated either from measured values for the airway pressure, volume flow Flow(t) (from which the tidal volume Vol(t) is also obtained by integration) as well as the lung mechanical parameters R (resistance) and E (elastance) in the control unit, or (II) by equating with the negative airway pressure $-p_{occl}(t)$ measured during an occlusion, where the lung mechanical parameters R and E are also either calculated or preset, or (III) by determining it by means of an esophageal catheter, which is equipped with pressure sensors for measuring the intrathoracic pressure $p_{es}(t)$ and optionally the abdominal pressure $p_{abd}(t)$, by equating with the transdiaphragmal pressure $p_{abd}(t)-p_{es}(t)$, where $p_{abd}(t)$ can be optionally assumed to be constant.

The breathing activity signal $u_{emg}(t)$ is subjected to transformation into a pressure signal $p_{emg}(u_{emg}(t))$ by means of a preset transformation rule, the transformation rule being selected such that the resulting $p_{emg}(t)$ corresponds in terms of signal size and shape, on average, to the $p_{mus}$ signal, i.e., the mean deviation between the pressure signals is minimal. The transformation rule can be determined by linear or non-linear regression between $u_{emg}(t)$ and $p_{mus}(t)$ or also according to other procedures, e.g., with neuronal networks, machine learning or simple scaling.

The respiratory effort pressure $p_{pat}(t)$ is determined by the control unit as a weighted mean according to $p_{pat}(t)=a \cdot p_{mus}(t)+(1-a) \cdot p_{emg}(t)$, in which a is a parameter selected under the boundary condition $0 \leq a \leq 1$. Depending on the parameter a selected, the pressure assist of the respiration system depends more strongly on $p_{mus}(t)$ or on $p_{emg}(t)$ as desired. If, for example, a tends towards 1, the respiration corresponds to the known proportional assist ventilation. The myographically controlled respiration prevails at low values of a.

The airway pressure $p_{aw}(t)$ to be delivered by the ventilator of the respiration system is calculated in the control unit as a function of the preselected degrees of assist VA (Volume Assist) for compensating the elastic restoring forces/resistances and FA (Flow Assist) for compensating the resistive restoring forces/resistances by sliding adaptation as $$p_{aw}(t_i) = k_0 + \sum_{j=1}^{n} k_j \cdot p_{aw}(t_{i-j}) + \sum_{j=0}^{n} h_j \cdot p_{pat}(t_{i-j})$$

in which $t_i$ is a current point in time and $t_{i-j}$, in which $j=1,\ldots,n$, are previous points in time of a periodical time-discrete sampling, and $k_j$ and $h_j$, in which $j=1,\ldots,n$ are parameters that depend on R, E, PEEP, iPEEP, VA and FA and the sampling time $\Delta t$. A simplified formula can be used in a preferred embodiment:

$$p_{aw}(t_i)=k_1 \cdot p_{aw}(t_{i-1})+k_2 \cdot p_{pat}(t_i)+k_3 \cdot p_{pat}(t_{i-1})+k_4.$$

Finally, the ventilator is set by the control unit so as to provide this airway pressure $p_{aw}(t)$.

In a preferred embodiment, the rate of change (time derivative) $\dot{u}_{emg}(t)$ of the breathing activity signal $u_{emg}(t)$ is checked in the control unit continuously to determine whether it is below a threshold value criterion, and a period of the breathing cycle that is constant with respect to the breathing activity is established for the duration of the period during which said value is below the threshold value; the lung mechanical parameter E (elastance) is then determined only from measured values that were recorded during a constant period.

In another preferred embodiment, the breathing activity signal $u_{emg}(t)$ is checked continuously in the control unit to determine whether it is below a threshold value criterion, and a period of the breathing cycle that is passive with respect to the breathing activity is established; the lung mechanical parameter E (elastance) is then determined only from measured values that were recorded during a passive period.

It is advantageous, in particular, that the method according to the present invention is a noninvasive method. It requires no invasive gastric probe equipped with electrodes, but makes do with surface electrodes or sensors for recording the respiratory muscle activity.

The method is hardly susceptible to a change in the coupling between the electrodes or sensors and the signal source, because a model-based signal of the breathing activity can be used in case of failure of electrodes or sensors.

It diminishes the risk of run-aways, because the mechanical parameters of the patient's lungs, which must be taken into account for setting the degree of assist, are determined robustly during spontaneous breathing.

It makes it possible to set the work of breathing to be performed by the patient by presetting a degree of support of the respiration. This may happen either separately for resistive and elastic work or jointly.

For example, the following linear regression equation $p_{mus}(t)=a_0+a_1 u_{emg}(t)+a_2 u^2_{emg}(t)+a_3 u^3_{emg}(t)+\epsilon(t)$ can be used to determine the regression coefficient for the transformation rule being sought. The coefficients $a_0$, $a_1$, $a_2$, $a_3$ are obtained after minimizing the sum of the squares of the deviations $\epsilon(t)$. To reduce errors in estimation, the coefficients obtained may be subjected to a sliding averaging. The transformation rule for the breathing activity signal $$u_{emg}(t) p_{emg}(t) = <a_0> + <a_1> u_{emg}(t) + <a_2> u^2_{emg}(t) + <a_3> u^3_{emg}(t)$$

is finally obtained from the current, averaged coefficients $<a_0>$, $<a_1>$, $<a_2>$, $<a_3>$, so that the transformed $p_{emg}(t)$ signal is finally obtained for use in the respiration control.

The non-linear activation characteristic of the diaphragm is taken into account by such a transformation of the amplitude values (see Goldmann, M. D. et al.: The Dynamic Properties of Mammalian Skeletal Muscles, *Journal of Applied Physiology*, 1978, 44(6): 840-848). FIG. 8 shows in an example the curves of $p_{mus}(t)$ and $u_{emg}(t)$ during two breaths. The axis scaling and the shape of the signals differ greatly. FIG. 9 shows the result of the transformation after application of the transformation rule for $p_{emg}(t)$ determined by means of regression.

Parameter a is set automatically during the determination of the respiratory effort pressure in a preferred embodiment. In particular, a is automatically increased when the quality of the transformed myographic signal $p_{emg}(t)$ decreases and reduced when the quality increases. Correlation measures can be used as an indicator of the quality of the myographic signal $p_{emg}(t)$. For example, the maximum of the correlation (Pearson correlation coefficient) between $p_{emg}(t)$ and the measured signals for the negative airway pressure, volume flow (Flow) and volume can be used as a standard for the quality of $p_{emg}(t)$. A numerical value towards 1 indicates a close correlation and could be expected in the case in which the myographic signal $p_{emg}(t)$ is affected by disturbances only slightly and reflects mainly respiratory muscle activity.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
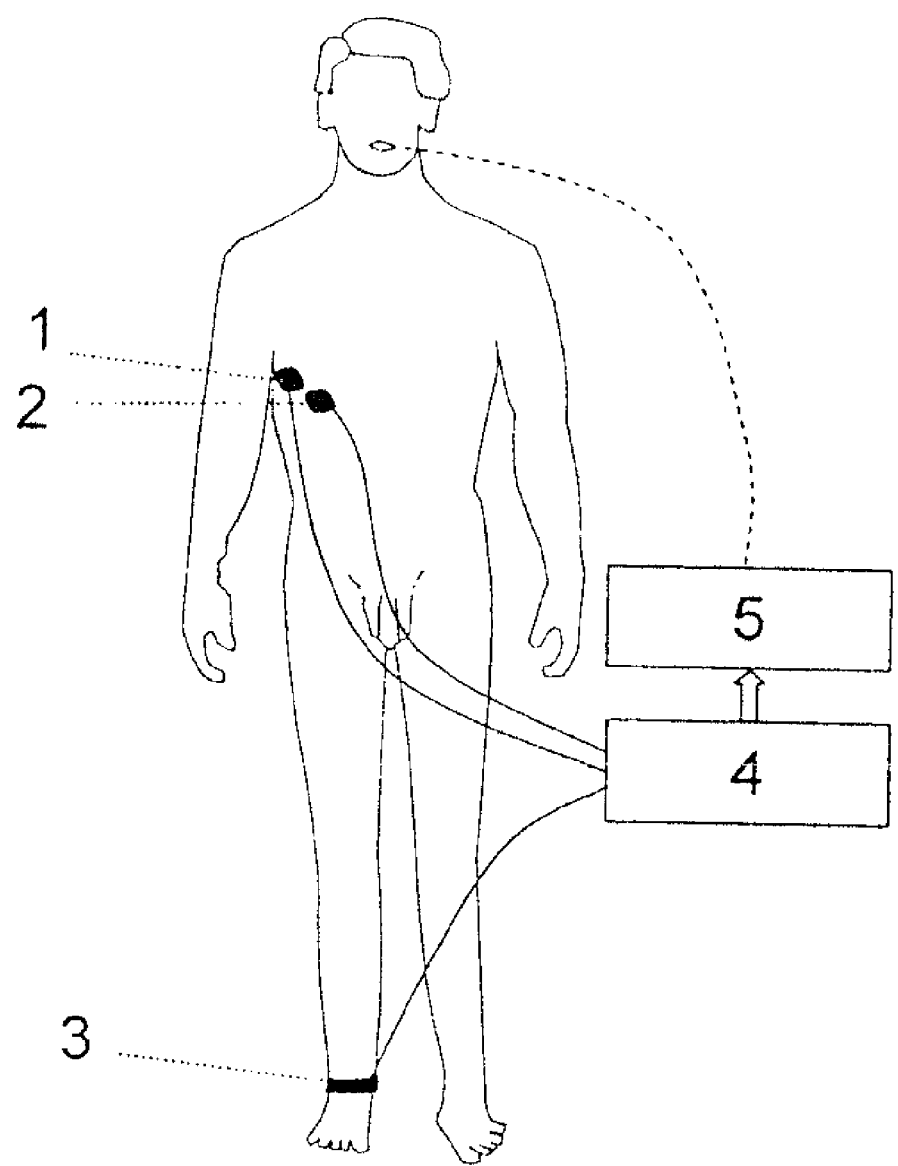
FIG. 1 is a schematic view of the arrangement of the two signal electrodes (1, 2) as well as of a driven right leg electrode (3) for the active common mode rejection of the interference signal on the body, the analysis means for the recorded signal (4) and the ventilator (5)

Referring to the drawings in particular, according to the present invention, the breathing activity signal can be recorded alternatively by electromyography or mechanomyography, both methods providing a signal representing the muscular exertion; a signal representing the electric excitation of the muscle in the first case and a signal representing the mechanical vibrations of the muscle in the second case. Reference will be made below mostly to the electromyographic alternative, and this should be understood such that it would alternatively also be possible to use mechanomyographic signals.

In an advantageous embodiment, the value of the breathing activity signal $u_{emg}(t)$ is checked continuously in the control unit to determine whether the signal is below another threshold value criterion, and a passive period of the breathing cycle is established for the duration of the period during which said signal is below said threshold value, and the other lung mechanical parameter elastance (E) is only determined from measured values that were recorded during a passive period.

In an advantageous embodiment, the electromyographic signal is derived as a difference signal between two surface electrodes (cf., e.g., Merletti, R.: Parker, A. P.: Electromyography, Physiology, Engineering, and Noninvasive Applications, IEEE Press Series Biomedical Engineering, John Wiley & Sons, 2004). To obtain a good signal-to-noise ratio, it may be necessary to use large, flat electrodes, with which summation in space of the action potentials of many motor units is achieved. FIG. 1 shows the positioning of two signal electrodes (1, 2) as well as of a driven right leg electrode (3) for the active common mode rejection of interference signals on the body, the analysis means for the recorded signal (4) and the ventilator (gas delivery device/fan unit) (5) in an exemplary embodiment.

Figure 2:
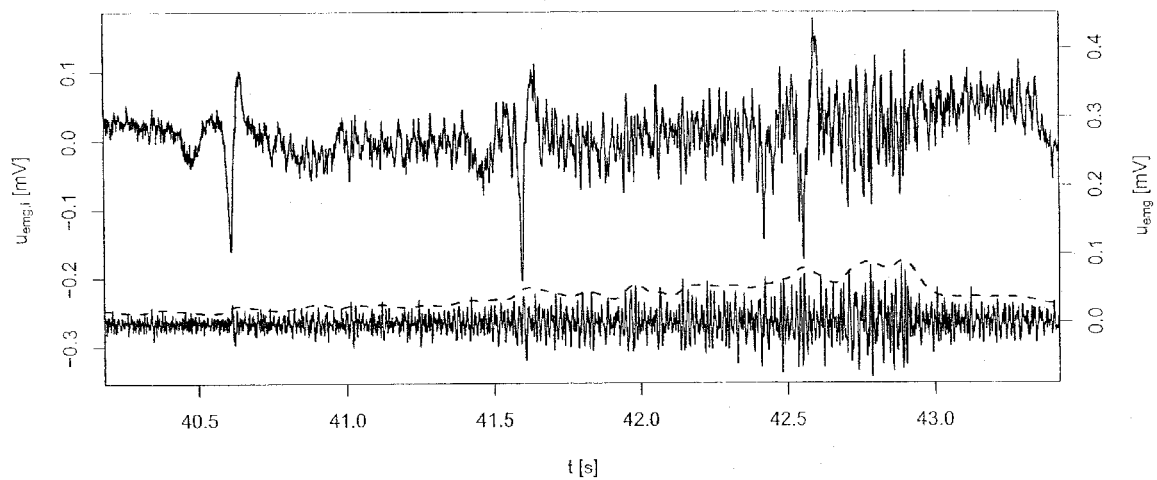
FIG. 2 is a view showing a non-processed electromyographic difference signal $u_{emg,i}(t)$ disturbed by cardiac activity as a function of time (top) and the result after a high-pass filtration (bottom, solid line; high-pass filtration by means of a third-order Butterworth filter, cut-off frequency 50 Hz) as well as subsequent quantity formation and low-pass filtration (bottom, broken line; low-pass filtration by means of third-order Butterworth filter, cut-off frequency 5 Hz) for determining the envelope (a signal thus processed will hereinafter be called a processed signal)

More than two surface electrodes are used to derive signals and difference signals are formed between two electrodes as breathing activity signals $u_{emg,i}$ in an advantageous embodiment. As an alternative, more than one sensor is used to derive mechanomyographic breathing activity signals $u_{emg,i}(t)$. Every individual signal $u_{emg,i}(t)$ is then preferably subjected to filtration and suppression of interference signals (e.g., electrical activity of the heart, motion artifacts, electromagnetic radiation) as well as to an envelope detection. The envelope detection is preferably carried out by quantity formation or squaring and subsequent low-pass filtration of every individual signal $u_{emg,i}(t)$. The exemplary result of a high-pass filtration as well as subsequent quantity formation and low-pass filtration is shown in FIG. 2.

The maximum of the correlation between the particular signal $u_{emg,i}(t)$ and the measured signals for the negative airway pressure, volume flow (Flow) and volume can be preferably calculated as $c_i$ for every individual signal $u_{emg,i}(t)$. The signal $u_{emg,i}(t)$ that shows the closest correlation $c_i$ and is therefore affected by disturbances only slightly and decisively reflects the patient's activity is then selected especially preferably.

As an alternative, the activity signal $u_{emg,i}(t)$ is calculated as a mean weighted with functions of the maximum correlations of the particular individual signals $u_{emg,i}(t)$:

$$u_{emg}(t)=f(c_1)\cdot u_{emg,1}(t)+\ldots+f(c_n)\cdot u_{emg,n}(t).$$

In an advantageous embodiment, the fact that the signal is below the threshold value criterion for the time derivative of the breathing activity signal $\dot{u}_{emg}(t)$ is established only if the signal remains below the threshold value criterion over a minimum duration. Signals that are accidentally below the threshold value criterion due to fluctuations of the time derivative of the breathing activity signal can thus be prevented from being erroneously interpreted as being constant sections.

The threshold value criterion for the time derivative of the breathing activity signal is adapted slidingly in an advantageous embodiment by determining a threshold value according to $\dot{u}_{thresh}=\dot{u}_{emg}^{min}+x\cdot(\dot{u}_{emg}^{max}-\dot{u}_{emg}^{min})$, and the fact that the signal is below the threshold value criterion is established if $\dot{u}_{emg}\leq\dot{u}_{thresh}$, in which $\dot{u}_{emg}^{max}$ and $\dot{u}_{emg}^{min}$ are the maximum and minimum of the time derivative of the breathing activity signal, respectively, which were measured during a previous interval and are adapted as soon as a new maximum or minimum signal value arises, and wherein x is a preselected parameter (0<x<1).

As an alternative, the threshold value criterion for the time derivative of the breathing activity signal is adapted slidingly by analyzing the measured value distribution $V(\dot{u}_{emg})$ and establishing the fact that the signal is below the threshold value criterion if a signal value $\dot{u}_{emg}$ is located within the distribution $V(\dot{u}_{emg})$ such that only p % of all measured values are at lower values within the distribution $V(u_{emg})$ (quantile of values below the threshold value criterion), wherein p is a preset parameter <100.

It would be possible, for example, to set the threshold at the simple standard deviation, i.e., at a value below which 84% of the signal values of $\dot{u}_{emg}$ are if normal distribution is assumed.

An adaptation of the threshold value criterion is preferably performed only when an analysis of the measured value distribution $V(\dot{u}_{emg})$ shows that scaling-invariant parameters of the distribution (e.g., skewness (skewness of the distribution), kurtosis (bulging of the distribution)) have remained essentially constant. This indicates that the shape of the distribution has remained the same and only the amplification (scaling) of the signal has changed, e.g., due to an altered coupling between the electrodes and the signal source. The threshold is thus prevented from shifting when the patient becomes more active or more passive for a rather long period of time, which is manifested in an altered shape of the distribution.

As an alternative, a fixed threshold value $\dot{u}_{thresh}$ is preset for the threshold value criterion, and the measured values are scaled such that the continuously updated maxima $\dot{u}_{emg}^{max}$ and minima $\dot{u}_{emg}^{min}$ of the time derivative of the breathing activity signal remain within a preset range of values.

The fact that the signal is below the other threshold value criterion for the breathing activity signal $u_{emg}(t)$ is established in an advantageous embodiment only if the signal remains below the threshold value criterion for a minimum duration. Signals that are accidentally below the threshold value criterion due to fluctuations of the time derivative of the breathing activity signal can thus be prevented from being erroneously interpreted as being passive sections.

In an advantageous embodiment, the other threshold value criterion for the breathing activity signal is adapted slidingly, determining a threshold value according to $$u_{thresh}=u_{emg}^{min}+x\cdot(u_{emg}^{max}-u_{emg}^{min})$$

and establishing the fact that the signal is below the threshold value criterion if $u_{emg}\leq u_{thresh}$, in which $u_{emg}^{max}$ and $u_{emg}^{min}$ are the maximum and minimum breathing activity signal values, respectively, which were measured during a previous interval and which are adapted as soon as a new maximum or minimum signal value arises, and wherein x is a preselected parameter (0<x<1).

The other threshold value criterion for the breathing activity signal is adapted slidingly in an advantageous embodiment by analyzing the measured value distribution $V(u_{emg})$ and establishing the fact that the signal is below the other threshold value criterion if a signal value $u_{emg}(t)$ is located within the distribution $V(u_{emg})$ such that only p % of all measured values are at lower values within the distribution $V(u_{emg})$ (quantile of values below the threshold value criterion), wherein p is a preset parameter <100.

Figure 3:
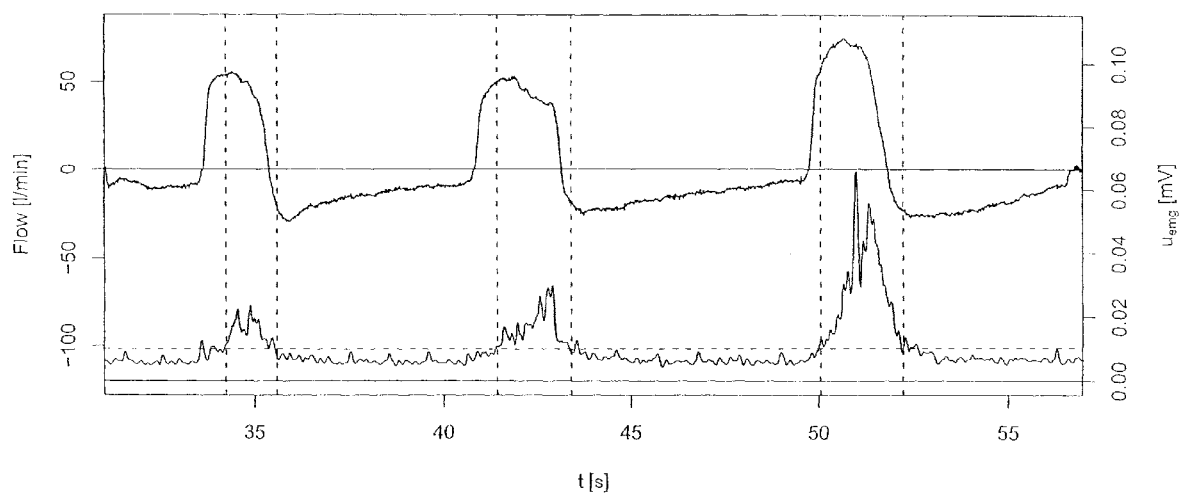
FIG. 3 is a view showing the patient's measured airway flow (top) as a function of the processed breathing activity signal $u_{emg}(t)$ (bottom)
Figure 4:
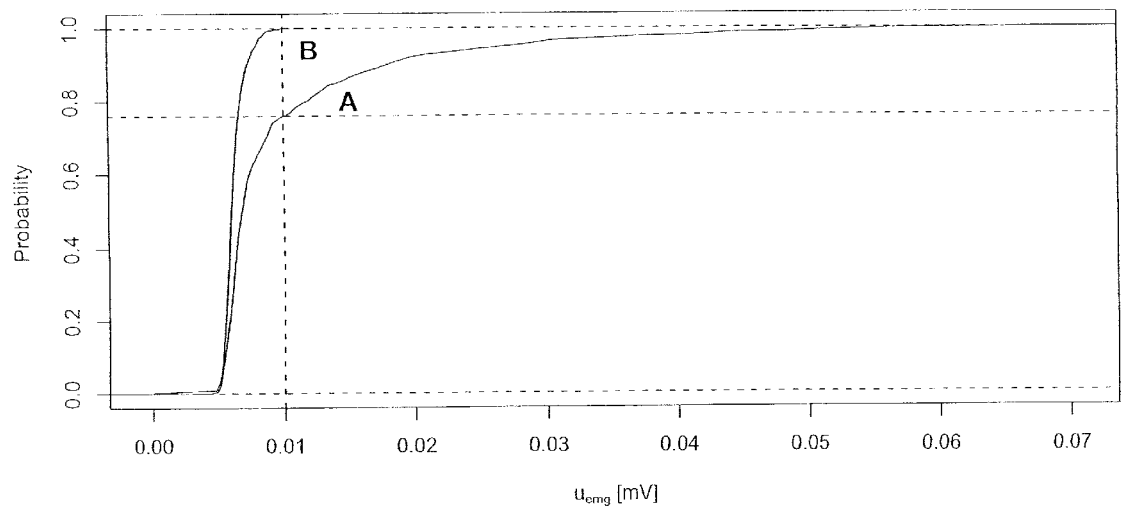
FIG. 4 is a view showing the empirical cumulative measured value distribution for the amplitudes of the signal $u_{emg}(t)$ during an active interval (A) as well as during a passive interval (B), the threshold being set, for example, at the 0.75th-order quantile, which corresponds to a signal value of 0.01 mV (vertical broken line)

FIG. 3 shows as an example the patient flow (top) and the breathing activity signal $u_{emg}(t)$ (bottom). Active ranges are defined by vertical broken lines, and passive ranges are located on the outside. The horizontal broken line marks the threshold. FIG. 4 shows the corresponding empirical cumulative measured value distribution for the amplitudes of the signal $u_{emg}(t)$ during an active interval (A) as well as, for comparison, during a passive time interval (B). The threshold is set, for example, at the 0.75th-order quantile, which corresponds to a signal value of 0.01 mV. This leads in (A) to a probability of 75% with which signal values remain below the threshold.

An adaptation of the other threshold value criterion is performed in an advantageous embodiment only if an analysis of the measured value distribution $V(u_{emg})$ reveals that scaling-invariant parameters of the distribution (e.g., skewness, kurtosis) have remained essentially unchanged. This indicates that the shape of the distribution has remained the same and only the amplification (scaling) of the signal has changed, e.g., due to an altered coupling between the electrodes and the signal source. The threshold is thus prevented from shifting when the patient becomes more active or more passive for a rather long period of time, which is manifested in an altered shape of the distribution.

As a consequence, an adaptation of the other threshold value criterion may be performed only if the shape of the probability density has not changed substantially. This can be decided by means of parametric statistical (significance) tests (see Krishnamurty Muralidhar: The bootstrap approach for testing skewness persistence, *Management Science*, 1993, 39(4), pp. 487-491).

Figure 5:
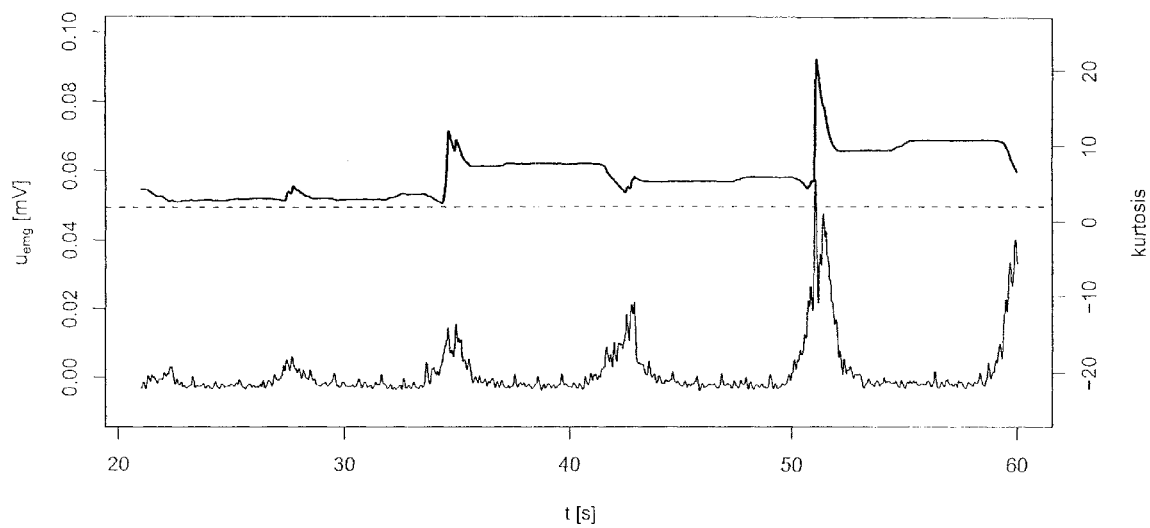
FIG. 5 is a view showing a measured processed breathing activity signal $u_{emg}(t)$ (bottom) and the calculated kurtosis during active spontaneous breathing (top)
Figure 6:
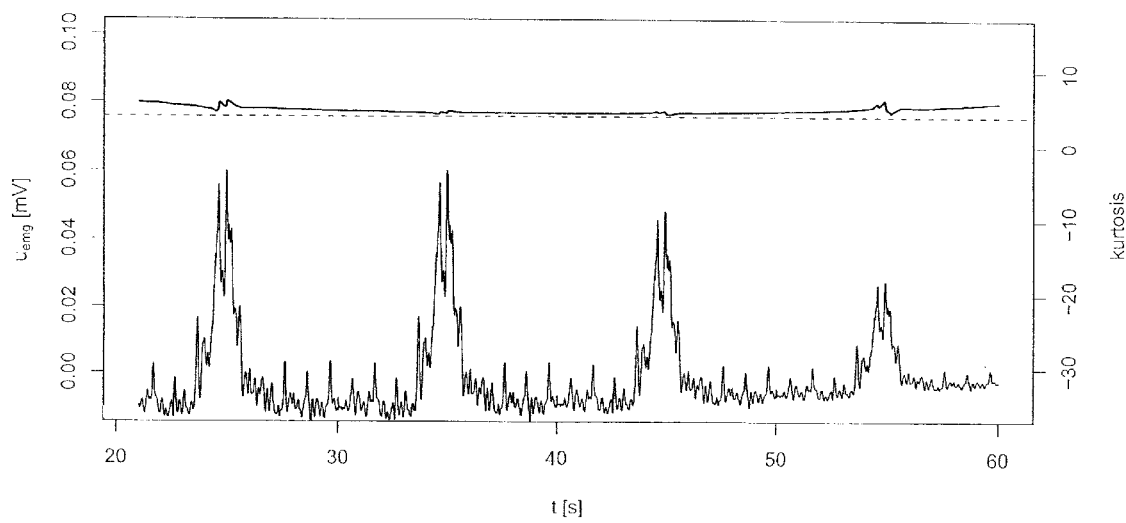
FIG. 6 is a view showing a processed breathing activity signal $u_{emg}(t)$ (bottom) during constant spontaneous breathing, but strong artificial amplitude distortion, which simulates deteriorating coupling, as well as the calculated kurtosis (top)

FIG. 5 shows as an example of a measured breathing activity signal $u_{emg}(t)$ and the calculated kurtosis during active spontaneous breathing. The kurtosis increases markedly with increasing spontaneous breathing (see deviation from the horizontal broken line). FIG. 6 correspondingly shows a breathing activity signal $u_{emg}(t)$ with constant spontaneous breathing, but strong artificial amplitude distortion, which simulates a deteriorating coupling. The calculated kurtosis is flat (only a slight deviation from the horizontal broken line), so that, contrary to FIG. 5, adaptation of the threshold value criterion would be meaningful.

As an alternative, a fixed threshold value $u_{thresh}$ is preset for the other threshold value criterion, and the measured values are scaled such that the continuously updated maxima and minima $u_{emg}^{max}$ and $u_{emg}^{min}$ of the breathing activity signal remain within a preset, fixed range of values.

In an advantageous embodiment, the lung mechanical parameter resistance (R) is determined by means of occlusion methods during a passive or constant period of the breathing cycle.

The lung mechanical parameter resistance (R) is determined in an advantageous embodiment by means of an end-expiratory occlusion or the special case of a p0.1 occlusion. No passive time periods are assumed here in the breathing pattern, but the patient is forced by a brief end-expiratory occlusion to actively request the next respiration stroke. A robust estimate can be obtained for the resistance from the pressure drop caused by the patient and the flow developing after the end of the occlusion.

In an advantageous embodiment, the lung mechanical parameter "intrinsic PEEP" (iPEEP) is determined by means of an end-expiratory occlusion or a p0.1 occlusion (see L. Appendini et al., Noninvasive estimation of dynamic intrinsic PEEP (PEEPi,dyn) in COPD patients, *Am. J. Respir. Crit. Care Med.*, 2003; 167 (7): A912).

The lung mechanical parameter elastance (E) is determined in an advantageous embodiment by determining the time constant τ during a passive period of the breathing cycle during inspiration or expiration according to E=R/τ, in which R is the resistance determined advance and τ is the respiratory time constant. The time constant is obtained as a quotient of the expired volume to the maximum expiratory flow according to $$\tau = V_T/\text{Flow}_{max}.$$

As an alternative, the lung mechanical parameter elastance (E) can be determined by regression between the administered volume and the alveolar pressure during a constant or passive period of inspiration or expiration. This is especially meaningful when respiratory efforts occur during the expiration, so that the entire phase of aspiration cannot be considered to be passive. Once a measured value is known for the resistance (R), the alveolar pressure necessary for the regression can be calculated according to $p_{alv}(t)=p_{aw}(t)-R\,\text{Flow}(t)$. The linear regression equation can thus be set up as $p_{alv}(t)=E\,\text{Vol}(t)+\text{const}+\epsilon(t)$. The elastance (E) is obtained after minimizing the sum of the squares of the deviations $\epsilon(t)$ within the constant or passive period.

Figure 7:
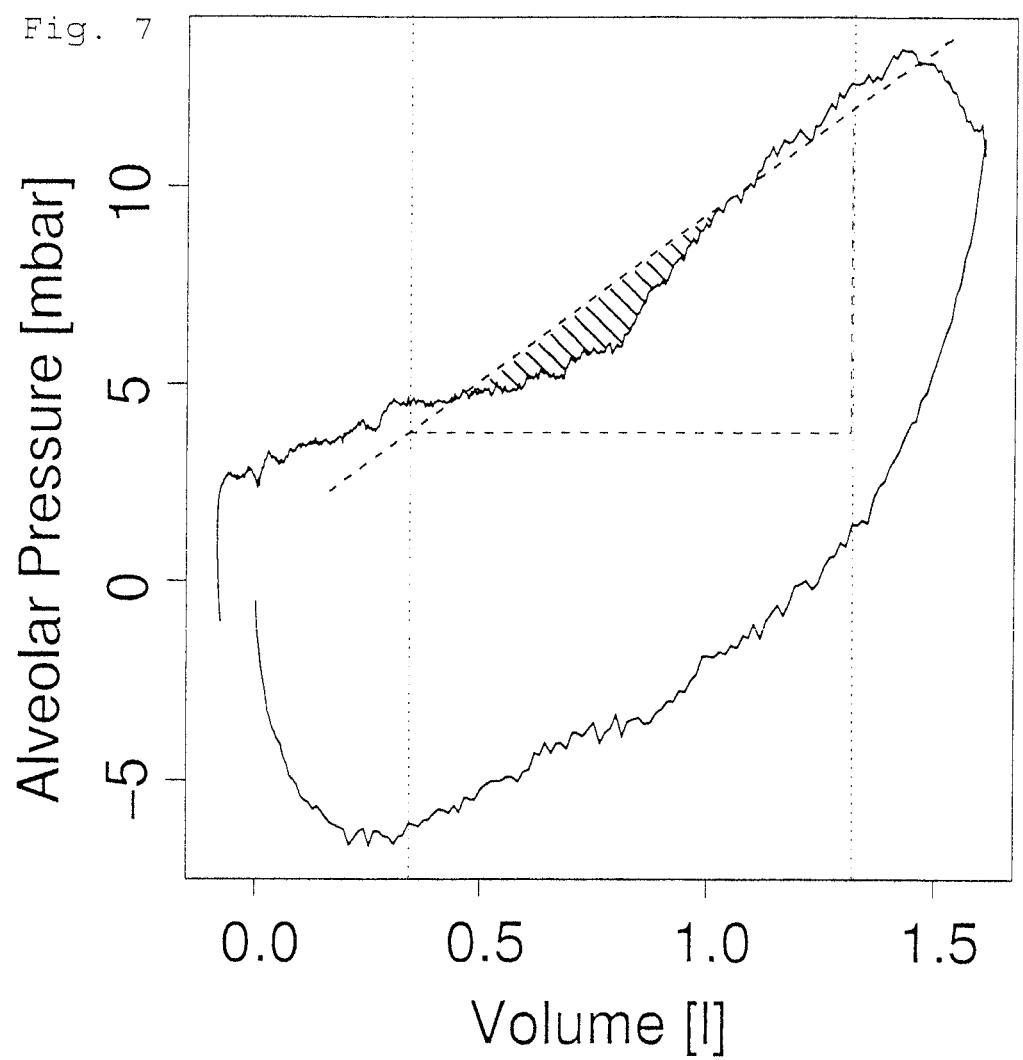
FIG. 7 is a view showing the regression for calculating the elastance (E) in an interval defined by vertical broken lines, wherein the ratio of the largest contiguous area between the curve and the regression line (shaded) to the area of the pitch triangle defined by the limits of the interval is used as a criterion for accepting or rejecting the calculated elastance.
Figure 8:
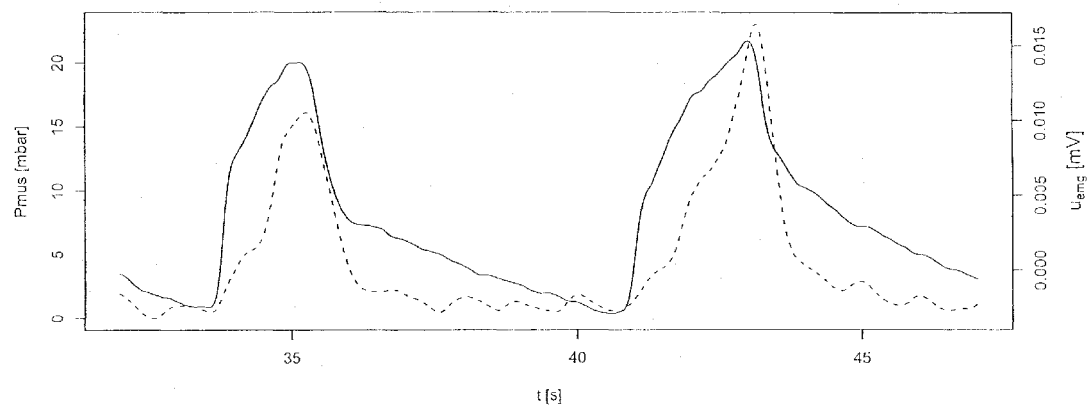
FIG. 8 is a view showing the curves of $p_{mus}(t)$ (solid line) and the processed $u_{emg}(t)$ (broken line) during two breaths.
Figure 9:
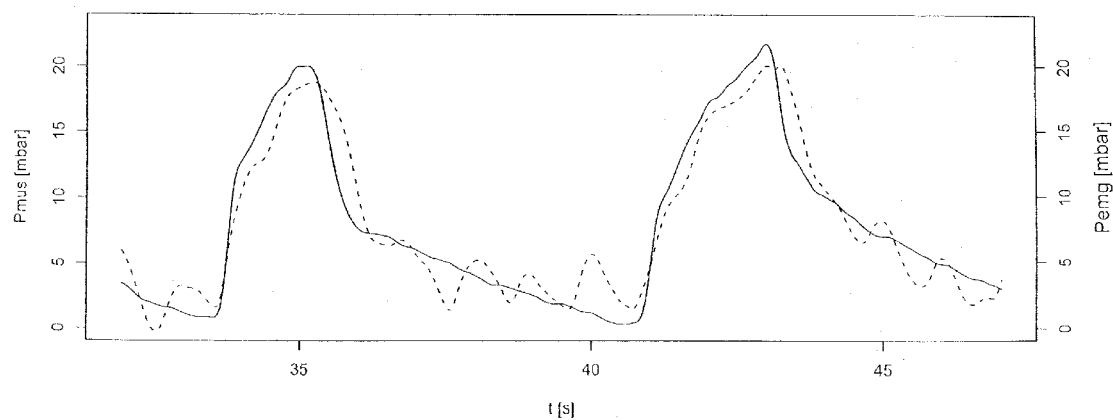
FIG. 9 is a view showing the curves of $p_{mus}(t)$ and of the result of the transformation, $p_{emg}(t)$ after application of the transformation rule $u_{emg}(t)$ determined by means of regression.

In an advantageous embodiment, the determined elastance (E) should be discarded if the curve of the alveolar pressure widely deviates from the regression line during the time period assumed to be constant or passive. A criterion, which relates the largest contiguous area between the curve and the regression line $A_{cont}$ to the area of the slope triangle $A_{triangle}$, can be used for this. The determined elastance is discarded if, e.g., the quotient $A_{cont}/A_{triangle}$ is greater than 0.2. FIG. 7 shows as an example the regression in an interval defined by vertical broken lines, the largest contiguous area between the curve and the regression line (shaded) and the slope triangle defined by the limits of the interval.

The lung mechanical parameters resistance (R), elastance (E) and intrinsic PEEP (iPEEP) are subjected to a sliding averaging each to determine time-based mean values <R>, <E>, <iPEEP>. The time curve $p_{mus}(t)$ can be calculated from these time-based mean values as $$p_{mus}(t)=-p_{aw}(t)+<R>\text{Flow}(t)+<E>\text{Vol}(t)+<iPEEP>.$$

In an advantageous embodiment, the breathing activity signal $u_{emg}(t)$ is subjected to a transformation into a pressure signal $p_{emg}(u_{emg}(t))$ with a preset parametrization, and the breathing activity signal $u_{emg}(t)$ is transformed such that the deviation of $p_{emg}(u_{emg}(t))$ from $p_{mus}(t)$ is minimized.

In an advantageous embodiment, the breathing activity signal $u_{emg}(t)$ is subjected to a transformation into a pressure signal $p_{emg}(u_{emg}(t))$ by means of a preset transformation rule, the transformation rule being found by linear or non-linear regression between $u_{emg}(t)$ and the measured negative airway pressure $-p_{occl}(t)$ during an occlusion.

In another advantageous embodiment, the breathing activity signal $u_{emg}(t)$ is subjected to a transformation into a pressure signal $p_{emg}(u_{emg}(t))$ by means of a preset transformation rule, the transformation rule being found by linear or non-linear regression between $u_{emg}(t)$ and the measured transdiaphragmal pressure $p_{abd}(t)-p_{es}(t)$.

The transformation may be carried out as a sliding transformation over consecutive (optionally partially overlapping) time periods. The transformation rule may be updated at intervals, and effects of interferences can be reduced by means of overlapping time periods or another averaging.

In preferred embodiments, the parameters $k_1, k_2, k_3, k_4$ are determined by $$k_1 = \frac{R-FA}{R-FA+(E-VA)\cdot\Delta t},$$

$$k_2 = \frac{FA+VA\cdot\Delta t}{R-FA+(E-VA)\cdot\Delta t},$$

$$k_3 = \frac{FA}{R-FA+(E-VA)\cdot\Delta t},$$

$$k_4 = \frac{(PEEP\cdot E-iPEEP\cdot VA)\cdot\Delta t}{R-FA+(E-VA)\cdot\Delta t}.$$

In preferred embodiments, the present invention makes possible the following:

One possible embodiment provides for a degree of assist to be selected either separately for compensating the resistive and elastic resistances of the respiratory system of the patient or by means of a higher-level degree of assist for joint compensation. While FA and VA are set separately in case of the separate assist, there is a single setter, whose value "PPSp" is preset, in general, between 0 (no assist) and 1 (ideal assist), in case of joint compensation. Values are thus finally obtained for Flow Assist (FA) and Volume Assist (VA) as follows:

$$FA=(R-R_{ideal})*PPSp$$

$$VA=(E-E_{ideal})*PPSp$$

in which $R_{ideal}$ and $E_{ideal}$ represent the values for resistance and elastance of the patient that are "ideal" from a medical point of view and must be stored in the respirator or likewise must be set.

The work of breathing to be performed by the patient (WOB—Work of Breathing)—as is usually defined as a pressure-time integral or as a pressure-volume integral—can be set by this procedure to a certain value depending on the degree of support. This may be carried out either separately for resistive and elastic work or jointly.

Figure 10:
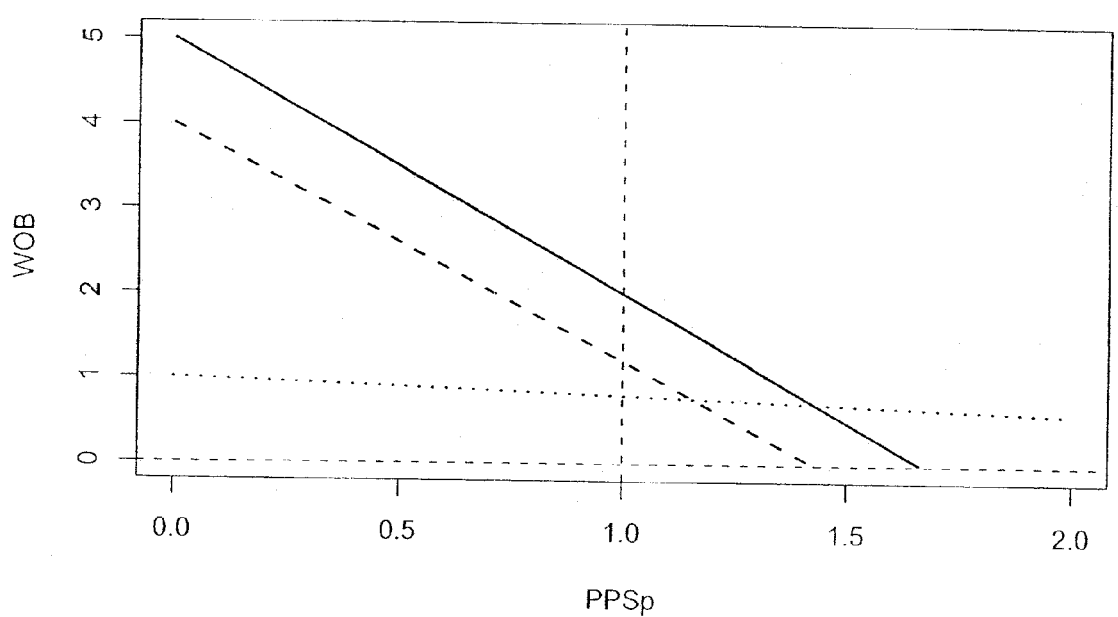
FIG. 10 is a schematic view showing the work of breathing as a function of the pressure assist, wherein the restrictive work of breathing is represented by the broken bold line and the elastic work of breathing by the dotted line and the total work of breathing by the solid line, and the value PPSp=1 marks the work of breathing that would have to be performed by the patient in the ideal case.

FIG. 10 shows this schematically for the latter case. The resistive work of breathing is represented by the bold broken line and the elastic work of breathing by the dotted line. The total work of breathing (sum of the resistive and elastic work) is indicated by a solid line. The unit of the work of breathing (WOB) is not shown in the schematic drawing. The work of breathing decreases in proportion to the increase in PPSp. The value PPSp=1 marks the work of breathing that would have to be performed by the patient in the ideal case (e.g., patient with healthy lungs). The PPSp must not be increased above a value of about 1.4 in this example, because there is otherwise the risk of run-aways due to overcompensation of the resistive work of breathing.

While specific embodiments of the invention have been shown and described in detail to illustrate the application of the principles of the invention, it will be understood that the invention may be embodied otherwise without departing from such principles.

What is claimed is:

1. A method of automatically controlling a respiration system for proportional assist ventilation of a subject with a control means and with a ventilator, which delivers a breathing gas with a pressure preset by the control unit, the method comprising the steps of:
    recording an electric signal using electrodes on the chest of the subject with the signal generated by electromyography or using sensors on the chest with the signal generated by mechanomyography;
    subjecting the signal to signal processing in the control means in order to obtain a signal $u_{emg}(t)$ representing the breathing activity;
    determining the respiratory muscle pressure $p_{mus}(t)$ by calculating $p_{mus}(t)$ from one of:
        measured values for an airway pressure and a volume flow Flow(t) as well as from the lung mechanical parameters of the patient in the control unit,
        the respiratory muscle pressure being equated with a negative airway pressure $-p_{occl}(t)$ measured during an occlusion, and
        determined values provided by means of an esophageal catheter, which is equipped with pressure sensors for measuring one or more of an intrathoracic pressure $p_{es}(t)$ and an abdominal pressure $p_{abd}(t)$, by equating with a transdiaphragmal pressure $p_{abd}(t)-p_{es}(t)$, where $p_{abd}(t)$ can be optionally assumed to be constant;
    transforming the breathing activity signal $u_{emg}(t)$ into a pressure signal $p_{emg}(u_{emg}(t))$ by means of a preset transformation rule, the transformation rule being determined such that a mean deviation of the resulting transformed pressure signal $p_{emg}(t)$ is minimized by the respiratory muscle pressure $p_{mus}(t)$ determined;
    determining a respiratory effort pressure $p_{pat}(t)$ by the control unit as a weighted mean according to $p_{pat}(t)=a \cdot p_{mus}(t)+(1-a) \cdot p_{emg}(t)$, in which a is a parameter selected under the boundary condition $0 \leq a \leq 1$;
    calculating the airway pressure $p_{aw}(t)$ to be delivered by the ventilator of the respiration system in the control unit by a sliding adaptation as a function of preselected degrees of assist VA Volume Assist (VA) for the compensation of elastic recoil forces/resistances and Flow Assist (FA) for a compensation of the resistive forces as $$p_{aw}(t_i) = k_0 + \sum_{j=1}^{n} k_j \cdot p_{aw}(t_{i-j}) + \sum_{j=0}^{n} h_j \cdot p_{pat}(t_{i-j})$$

in which $t_i$ is a current point in time and $t_{i-j}$, j=1, ..., n, are previous points in time of a periodical time-discrete sampling and $k_j$ and $h_j$, in which j=1, ..., n, are parameters dependent on resistance (R), elastance (E), positive end-expiratory pressure (PEEP), intrinsic PEEP (iPEEP), VA, FA and the sampling time $\Delta t$, and the ventilator is set by the control unit so as to provide said airway pressure $p_{aw}(t_i)$.

2. A method in accordance with claim 1, wherein the respiratory muscle pressure $p_{mus}(t)$ is calculated on the basis of the lung mechanical parameters resistance (R), elastance (E) and optionally the value for the iPEEP, the lung mechanical parameters R and E being either calculated or preset.

3. A method in accordance with claim 1, wherein the airway pressure $p_{aw}(t)$ is calculated in the control unit by sliding adaptation as $$p_{aw}(t_i)=k_1 \cdot p_{aw}(t_{i-1})+k_2 \cdot p_{pat}(t_i)+k_3 \cdot p_{pat}(t_{i-1})+k_4.$$

4. A method in accordance with claim 1, wherein the preset transformation rule is defined by linear or non-linear regression, by means of neuronal networks, machine learning or by simple scaling.

5. A method in accordance with claim 1, wherein the rate of change (time derivative) $\dot{u}_{emg}$ of the breathing activity signal $u_{emg}(t)$ is continuously checked in the control unit to determine whether said breathing activity signal is below a threshold value criterion and the period of the breathing cycle that is constant with respect to the breathing activity is established for the duration of the period during which the signal is below the threshold value criterion, wherein the lung mechanical parameters E (elastance) or/and the lung mechanical parameter R (resistance) is only determined from measured values that were recorded during a constant period.

6. A method in accordance with claim 5, wherein the value of the breathing activity signal $u_{emg}(t)$ is continuously checked in the control unit to determine whether the signal is below another threshold value criterion and a passive period of the breathing cycle is established for the duration of the period during which the signal is below said another threshold value criterion, wherein the other lung mechanical parameter elastance (E) or/and the lung mechanical parameter R (resistance) is determined only from measured values that were recorded during a passive period.

7. A method in accordance with claim 1, wherein an electromyographic signal is derived as a difference signal between two surface electrodes.

8. A method in accordance with claim 7, wherein more than two surface electrodes are used to derive electromyographic signals and difference signals are formed between two electrodes as breathing activity signals $u_{emg,i}$.

9. A method in accordance with claim 1, wherein more than one sensor is used to derive mechanomyographic breathing activity signals $u_{emg}(t)$.

10. A method in accordance with claim 8, wherein every individual signal $u_{emg}(t)$ is subjected to filtering and interference signal suppression as well as to envelope detection.

11. A method in accordance with claim 10, wherein the envelope detection is carried out by taking the absolute value or squaring and subsequent low-pass filtering of every individual signal $u_{emg,i}(t)$.

12. A method in accordance with claim 1, wherein a maximum of the correlation between a particular signal $u_{emg,i}$ and the measured signals for the negative airway pressure, volume flow (Flow) and volume is calculated as $c_i$ for every individual signal $u_{emg,i}(t)$.

13. A method in accordance with claim 12, wherein the signal $u_{emg,i}(t)$ that has the closest correlation $c_i$ is selected as the breathing activity signal $u_{emg}(t)$.

14. A method in accordance with claim 11, wherein the activity signal $u_{emg}(t)$ is calculated as a mean weighted with functions of the maximum correlations of the particular individual signals $u_{emg,i}(t)$:

$$u_{emg}(t) = f(c_1) \cdot u_{emg,1}(t) + \ldots + f(c_n) \cdot u_{emg,n}(t).$$

15. A method in accordance with claim 5, wherein a state of the signal being below the threshold value criterion for the time derivative of the breathing activity signal $\dot{u}_{emg}(t)$ is determined only if the state of the signal is below the threshold value criterion and the state persists for a minimum duration.

16. A method in accordance with claim 5, wherein the threshold value criterion for the time derivative of the breathing activity signal is adapted slidingly by determining a threshold value according to $\dot{u}_{thresh} = \dot{u}_{emg}^{min} + x \cdot (\dot{u}_{emg}^{max} - \dot{u}_{emg}^{min})$ and determining the state of the signal is below the threshold value criterion if $\dot{u}_{emg} \leq \dot{u}_{thresh}$, wherein $\dot{u}_{emg}^{max}$ and $\dot{u}_{emg}^{min}$ are the maximum and the minimum of the time derivative of the breathing activity signal, respectively, which are measured in a previous interval and which are adapted as soon as a new maximum or minimum signal value is obtained, and wherein x is a preselected parameter ($0<x<1$)

17. A method in accordance with claim 5, wherein the threshold value criterion for the time derivative of the breathing activity signal is adapted slidingly by analyzing the measured value distribution $V(\dot{u}_{emg})$ and upon the state of the signal being below the threshold value criterion when a signal value $\dot{u}_{emg}$ is located within the distribution such that only p % of all measured values are located at lower values within the distribution $V(u_{emg})$ (quantile of values below the threshold value criterion), wherein p is a preset parameter <100.

18. A method in accordance with claim 16, wherein an adaptation of the threshold value criterion is performed only if an analysis of the measured value distribution $V(\dot{u}_{emg})$ shows that scaling-invariant parameters of the distribution have remained essentially constant.

19. A method in accordance with claim 5, wherein a fixed threshold value $\dot{u}_{thresh}$ is preset for the threshold value criterion, and the measured values are scaled such that the continuously updated maxima and minima $\dot{u}_{emg}^{max}$ and $\dot{u}_{emg}^{min}$ of the time derivative of the breathing activity signal remain within a preset, fixed range of values.

20. A method in accordance with claim 6, wherein the state of the signal being below said another threshold value criterion is established for the breathing activity signal $u_{emg}(t)$ only if the signal is below the threshold value criterion for a minimum duration.

21. A method in accordance with claim 6, wherein said another threshold value criterion for the breathing activity signal is adapted slidingly by determining a threshold value according to $u_{thresh} = u_{emg}^{min} + x \cdot (u_{emg}^{max} - u_{emg}^{min})$ and establishing a state with the signal below the threshold value criterion if $u_{emg} \leq u_{thresh}$, wherein $u_{emg}^{max}$ and $u_{emg}^{min}$ are the maximum and minimum breathing activity signal values, respectively, which were measured in a previous interval and which are adapted as soon as a new maximum or minimum signal value is obtained, and wherein x is a preselected parameter ($0<x<1$).

22. A method in accordance with claim 6, wherein said another threshold value criterion for the breathing activity signal is adapted slidingly by analyzing the measured value distribution $V(u_{emg})$ and establishing the state that the signal is below said another threshold value criterion if a signal value $u_{emg}(t)$ is located within the distribution $V(u_{emg})$ such that only p % of all measured values are located at lower values within the distribution $V(u_{emg})$ (quantile of values below the threshold value criterion), wherein p is a preset parameter <100.

23. A method in accordance with claim 21, wherein adaptation of the other threshold value criterion is performed only if an analysis of the measured value distribution $V(u_{emg})$ shows that scaling-invariant parameters of the distribution (e.g., skewness, kurtosis) have remained essentially constant.

24. A method in accordance with claim 6, wherein a fixed threshold value $u_{thresh}$ is preset for said another threshold value criterion and the measured values are scaled such that the continuously updated maxima and minima $u_{emg}^{max}$ and $u_{emg}^{min}$ of the breathing activity signal remain within a preset, fixed range of values.

25. A method in accordance with claim 1, wherein the lung mechanical parameter resistance (R) is determined by means of occlusion methods during a passive or constant period of the breathing cycle.

26. A method in accordance with claim 1, wherein the lung mechanical parameter resistance (R) is determined by means of an end-expiratory occlusion.

27. A method in accordance with claim 1, wherein the lung mechanical parameter "intrinsic PEEP" (iPEEP) is determined by means of an end-expiratory occlusion.

28. A method in accordance with claim 6, wherein the lung mechanical parameter elastance (E) is determined by determining a respiratory time constant $\tau$ during a passive period of the breathing cycle during inspiration or expiration according to $E = R/\tau$, wherein R is the resistance determined in advance.

29. A method in accordance with claim 5, wherein the lung mechanical parameter elastance (E) is determined by regression between the volume administered and the calculated alveolar pressure $p_{alv}(t) = p_{aw}(t) - R \cdot Flow(t)$ during a constant or passive period of inspiration or expiration.

30. A method in accordance with claim 1, wherein the lung mechanical parameters resistance (R), elastance (E) and intrinsic PEEP (iPEEP) are subjected each to a sliding averaging to determine time-based mean values <R>, <E>, <iPEEP>.

31. A method in accordance with claim 1, wherein an end-expiratory occlusion is used to determine the transformation rule.

32. A method in accordance with claim 31, wherein a p0.1 occlusion, corresponding to an occlusion for a time of 0.1 sec, is used as the end-expiratory occlusion.

33. A method in accordance with claim 3, wherein parameter $k_1$ is determined according to $$k_1 = \frac{R - FA}{R - FA + (E - VA) \cdot \Delta t}.$$

34. A method in accordance with claim 3, wherein parameter $k_2$ is determined according to $$k_2 = \frac{FA + VA \cdot \Delta t}{R - FA + (E - VA) \cdot \Delta t}.$$

35. A method in accordance with claim 3, wherein parameter $k_3$ is determined according to $$k_3 = \frac{FA}{R - FA + (E - VA) \cdot \Delta t}.$$

36. A method in accordance with claim 3, wherein parameter $k_4$ is determined according to $$k_4 = \frac{(PEEP \cdot E - iPEEP \cdot VA) \cdot \Delta t}{R - FA + (E - VA) \cdot \Delta t}.$$

37. A respirator comprising:
a ventilator for supplying breathing gas with an adjustable pressure;
electromyographic or mechanomyographic sensors for recording a breathing activity signal $u_{emg}(t)$;
a measured value recording means for recording measured values for an airway pressure and volume flow Flow(t) and for determining a tidal volume Vol(t);
a control and analysis unit for:
determining a respiratory muscle pressure $p_{mus}(t)$ using the signals determined for the breathing activity $u_{emg}(t)$, airway pressure and volume flow by calculating $p_{mus}(t)$ either (I) from measured values for the airway pressure and the volume flow Flow(t) as well as the patient's lung mechanical parameters, or (II) by determining $p_{mus}(t)$ by equating with the negative airway pressure $-p_{occl}(t)$ measured during an occlusion, or (III) by determining $p_{mus}(t)$ by means of an esophageal catheter, which is equipped with pressure sensors for measuring an intrathoracic pressure $p_{es}(t)$ and optionally an abdominal pressure $p_{abd}(t)$, by equating with a transdiaphragmal pressure $p_{abd}(t)-p_{es}(t)$, wherein $p_{abd}(t)$ can be optionally assumed to be constant;
transforming the breathing activity signal $u_{emg}(t)$ by means of a preset transformation rule into a pressure signal $p_{emg}(u_{emg}(t))$, wherein the transformation rule is determined such that a mean deviation of the resulting transformed pressure signal $p_{emg}(t)$ of the determined respiratory muscle signal $p_{mus}(t)$ is minimized;
determining a respiratory effort pressure $p_{pat}(t)$ as a weighted mean according to $p_{pat}(t)=a \cdot p_{mus}(t)+(1-a) \cdot pa_{emg}(t)$, wherein a is a parameter selected under the boundary condition $0 \leqq a \leqq 1$;
calculating the airway pressure $p_{aw}(t)$ to be delivered by said ventilator as a function of preselected degrees of Volume Assist (VA) for compensation of elastic recoil forces/resistances and Flow Assist (FA) for compensation of the resistive forces by sliding adaptation by $$p_{aw}(t_i) = k_0 + \sum_{j=1}^{n} k_j \cdot p_{aw}(t_{i-j}) + \sum_{j=0}^{n} h_j \cdot p_{pat}(t_{i-j})$$

wherein $t_i$ is a current point in time and $t_{i-j}$, wherein j=1, ..., n, are previous points in time of a periodical time-discrete sampling, and $k_j$ and $h_j$, wherein j=1, ..., n are parameters dependent on resistance (R), elastance (E), positive end-expiratory pressure (PEEP), intrinsic PEEP (iPEEP), VA, FA and the sampling time $\Delta t$, and to set the ventilator so as to provide this airway pressure $p_{aw}(t_i)$.

* * * * *